United States Patent
Liu

(10) Patent No.: US 10,402,158 B1
(45) Date of Patent: Sep. 3, 2019

(54) ELECTRONIC SYSTEM AND AUDIO PROCESSING METHOD

(71) Applicant: ACER INCORPORATED, New Taipei (TW)

(72) Inventor: Feng-Ming Liu, New Taipei (TW)

(73) Assignee: ACER INCORPORATED, New Taipei (TW)

( * ) Notice: Subject to any disclaimer, the term of this patent is extended or adjusted under 35 U.S.C. 154(b) by 0 days.

(21) Appl. No.: 16/164,728

(22) Filed: Oct. 18, 2018

(30) Foreign Application Priority Data

Jul. 17, 2018 (TW) .............................. 107124579 A

(51) Int. Cl.
| | |
|---|---|
| G06F 3/16 | (2006.01) |
| H04R 3/04 | (2006.01) |
| H03G 5/16 | (2006.01) |
| A61B 5/0476 | (2006.01) |
| A61B 5/04 | (2006.01) |
| A61B 5/0402 | (2006.01) |
| H04R 29/00 | (2006.01) |
| A61B 5/00 | (2006.01) |

(52) U.S. Cl.
CPC ............ *G06F 3/165* (2013.01); *A61B 5/0402* (2013.01); *A61B 5/04012* (2013.01); *A61B 5/0476* (2013.01); *H03G 5/165* (2013.01); *H04R 3/04* (2013.01); *H04R 29/001* (2013.01); *A61B 5/7257* (2013.01); *A61B 5/7271* (2013.01); *A61B 5/7415* (2013.01); *A61B 2503/12* (2013.01)

(58) Field of Classification Search
CPC ... G06F 3/165; A61B 5/04012; A61B 5/0402; A61B 5/0476; A61B 2503/12; A61B 5/7257; A61B 5/7271; A61B 5/7415; H03G 5/165; H04R 3/04; H04R 29/001
See application file for complete search history.

(56) References Cited

U.S. PATENT DOCUMENTS

| | | | | |
|---|---|---|---|---|
| 4,883,067 A | * | 11/1989 | Knispel | A61B 5/0482 600/545 |
| 7,979,130 B2 | * | 7/2011 | Carlson | A61B 5/02405 607/45 |
| 2005/0250996 A1 | * | 11/2005 | Shirai | A61B 3/113 600/301 |

(Continued)

FOREIGN PATENT DOCUMENTS

| | | | |
|---|---|---|---|
| KR | 20090066799 A | * | 6/2009 |
| TW | 201602826 A | | 1/2016 |

(Continued)

*Primary Examiner* — Davetta W Goins
*Assistant Examiner* — Kuassi A Ganmavo
(74) *Attorney, Agent, or Firm* — Winston Hsu

(57) ABSTRACT

An electronic system and an audio processing method are provided. The electronic system includes a physiological signal sensor, a processing circuit, an audio processing circuit and an audio output device. The physiological signal sensor is utilized for measuring a physiological signal of a user. The processing circuit is utilized for determining an audio setting according to the physiological signal. The audio processing circuit is utilized for receiving an audio signal and adjusting the audio signal according to the audio setting so as to generate an audio output signal. The audio output circuit is utilized for playing the audio output signal.

5 Claims, 5 Drawing Sheets

(56) References Cited

U.S. PATENT DOCUMENTS

| | | | |
|---|---|---|---|
| 2006/0084551 A1* | 4/2006 | Volpe, Jr. | A63B 71/0686 |
| | | | 482/8 |
| 2011/0188664 A1* | 8/2011 | Morikawa | A61B 5/04845 |
| | | | 381/60 |
| 2014/0105436 A1* | 4/2014 | Adachi | A61B 5/04845 |
| | | | 381/321 |
| 2014/0223462 A1* | 8/2014 | Aimone | A61B 5/0476 |
| | | | 725/10 |
| 2015/0283394 A1 | 10/2015 | Schmidt | |
| 2016/0286297 A1* | 9/2016 | Wang | H04R 1/1016 |

FOREIGN PATENT DOCUMENTS

| | | |
|---|---|---|
| TW | 201714460 A | 4/2017 |
| TW | 201724090 A | 7/2017 |

* cited by examiner

ELECTRONIC SYSTEM AND AUDIO PROCESSING METHOD

BACKGROUND OF THE INVENTION

1. Field of the Invention

The present invention relates to an electronic system and an audio processing method, and more specifically to a t an electronic system and an audio processing method capable of dynamically adjusting sound field effect in real-time.

2. Description of the Prior Art

With rapid development of technology, portable electronic devices equipped with multimedia playback functions, such as wearable devices, mobile phones, notebooks, tablets, portable audio players, are widely used in the daily life. In general, audio signals can be generated by the portable electronic devices and played back via audio output devices. However, if the same sound field setting is applied for playing back all audio signals, a user may easily feel tedious or boring when listening to the audio signals. Thus, the prior art has to be improved.

SUMMARY OF THE INVENTION

It is therefore a primary objective of the present invention to provide an electronic system and an audio processing method capable of dynamically adjusting sound field effect in real-time.

According to an embodiment of the present invention, an exemplary electronic system is disclosed. The exemplary electronic system comprises a physiological signal sensor, a processing circuit, an audio processing circuit and an audio output device. The physiological signal sensor is utilized for measuring a physiological signal of a user. The processing circuit is utilized for determining an audio setting according to the physiological signal. The audio processing circuit is utilized for receiving an audio signal and adjusting the audio signal according to the audio setting so as to generate an audio output signal. The audio output circuit is utilized for playing the audio output signal.

According to an embodiment of the present invention, an exemplary audio processing method is disclosed. The exemplary audio processing method comprises the following steps: measuring a physiological signal of a user; determining an audio setting according to the physiological signal; receiving an audio signal and adjusting the audio signal according to the audio setting so as to generate an audio output signal; and playing the audio output signal.

These and other objectives of the present invention will no doubt become obvious to those of ordinary skill in the art after reading the following detailed description of the preferred embodiment that is illustrated in the various figures and drawings.

DETAILED DESCRIPTION

Certain terms are used throughout the description and following claims to refer to particular components. As one skilled in the art will appreciate, hardware manufacturers may refer to a component by different names. This document does not intend to distinguish between components that differ in name but not function. In the following description and in the claims, the terms "include" and "comprise" are utilized in an open-ended fashion, and thus should be interpreted to mean "include, but not limited to . . . ". Also, the term "couple" is intended to mean either an indirect or direct electrical connection. Accordingly, if one device is coupled to another device, that connection may be through a direct electrical connection, or through an indirect electrical connection via other devices and connections.

Figure 1:
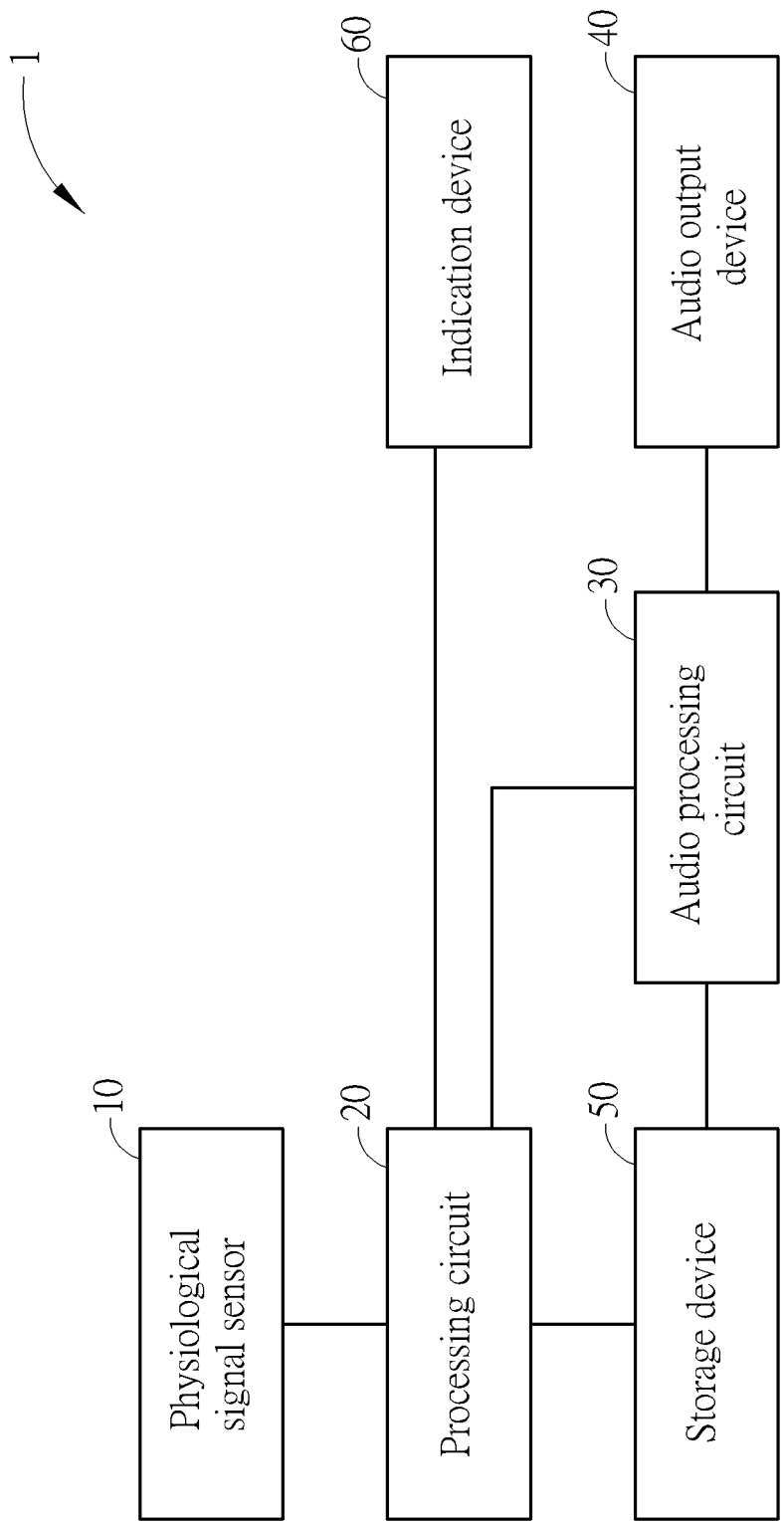
FIG. 1 is a schematic diagram of an electronic system according to an embodiment of the present invention.

Please refer to FIG. 1, which is a schematic diagram of an electronic system 1 according to an embodiment of the present invention. The electronic system 1 can be applied in various electronic products, such as headphone systems, speaker systems, mobile communication devices, notebooks, wearable devices, head-mounted devices, but not limited thereto. The electronic system 1 includes a physiological signal sensor 10, a processing circuit 20, an audio processing circuit 30, an audio output device 40, a storage device 50 and an indication device 60. The physiological signal sensor 10 is utilized for measuring a physiological signal of a user. The physiological signal sensor 10 can be an electroencephalogram (EEG) device, an electrocardiogram (ECG or EKG) device, a heart rate variability (HRV) monitor, a temperature sensor, an image sensor, an infrared sensor or a pressure sensor, but not limited thereto. The physiological signal measured by the physiological signal sensor 10 may be an EEG signal (also known as brain wave signal), an ECG signal, a heart rate signal, an HRV signal, a pulse signal, a blood pressure signal, a body temperature signal, a respiratory rate signal, but not limited thereto.

The processing circuit 20 is utilized for determining an audio setting according to the physiological signal measured by the physiological signal sensor 10. The processing circuit 20 can be a microprocessor control unit (MCU), but not limited thereto. The audio processing circuit 30 is utilized for receiving an audio signal and adjusting the audio signal according to the audio setting determined by the processing circuit 20, so as to generate an audio output signal. The audio processing circuit 30 can be a digital signal processor (DSP), but not limited thereto. The audio output device 40 is utilized for playing the audio output signal. The audio output device 40 can be a headphone or a speaker, but not limited thereto. The storage device can be any device capable of storing data.

Figure 2:
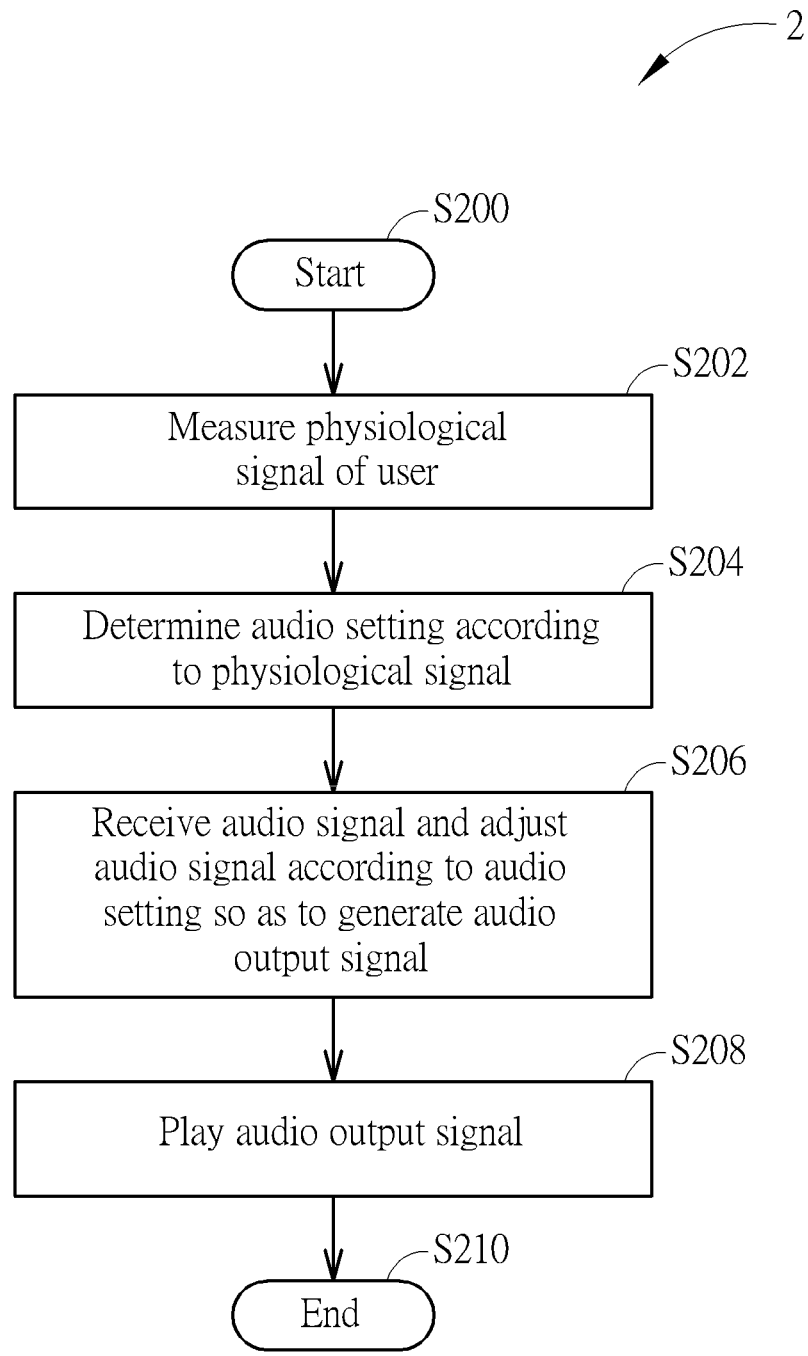
FIG. 2 is a schematic diagram of a procedure according to an embodiment of the present invention.

For an illustration of the operations of the electronic system 1, please refer to FIG. 2. FIG. 2 is a schematic diagram of a procedure 2 according to an exemplary embodiment of the invention. The procedure 2 includes the following steps:

Step S200: Start.
Step S202: Measure physiological signal of user.
Step S204: Determine audio setting according to physiological signal.
Step S206: Receive audio signal and adjust audio signal according to audio setting so as to generate audio output signal.

Step S208: Play audio output signal.

Step S210: End.

According to the procedure 2, in Step S202, the physiological signal sensor measures a physiological signal of a user during operation of the electronic system 1.

In Step S204, the processing circuit 20 determines an audio setting according to the physiological signal measured by the physiological signal sensor 10. For example, if the physiological signal sensor is an EEG device and the physiological signal measured by the physiological signal sensor 10 is an EEG signal. The processing circuit 20 determines an audio setting according to the EEG signal measured by the physiological signal sensor 10.

Figure 3:
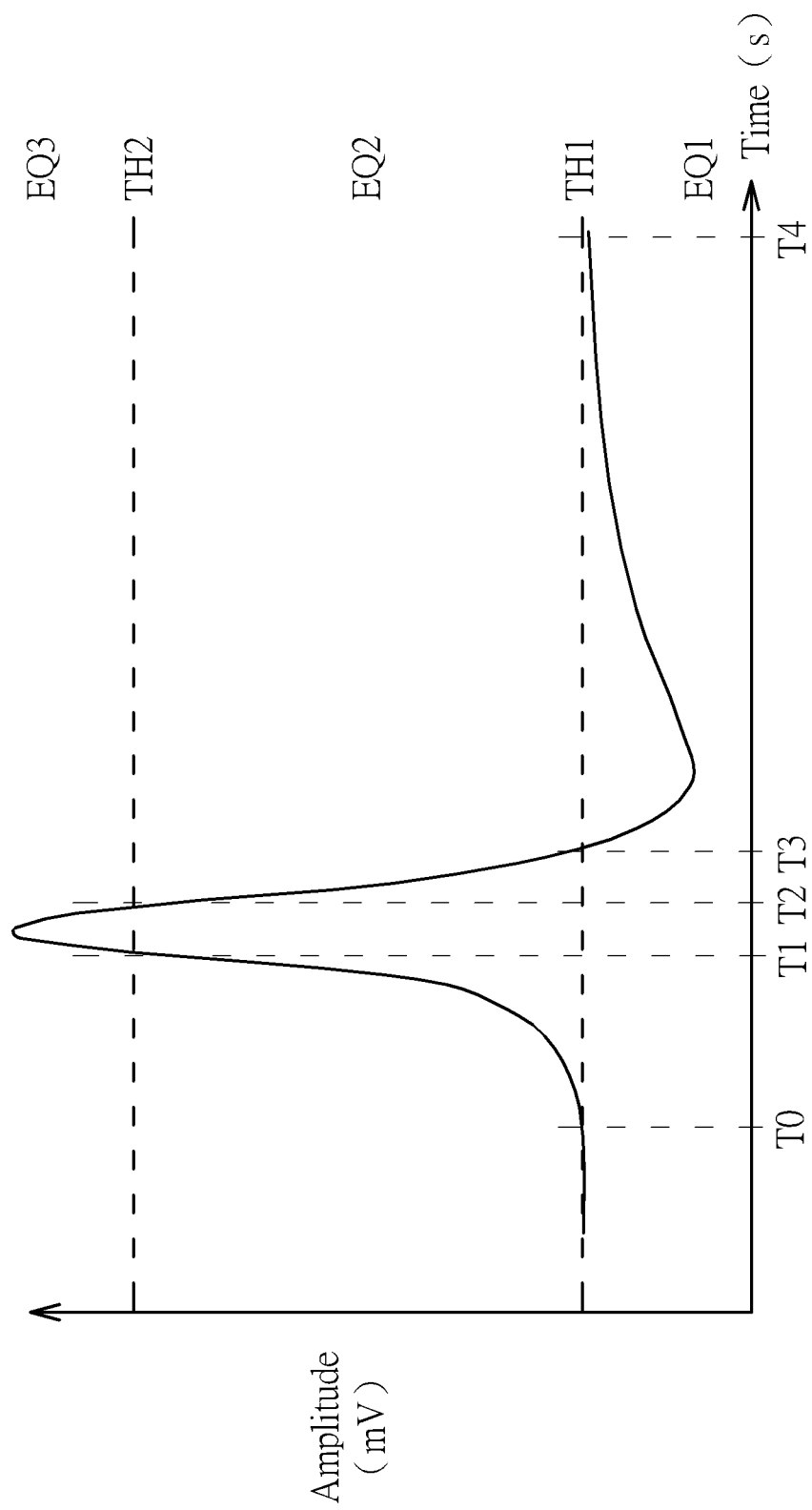
FIG. 3 is a schematic diagram of an EEG signal according to an embodiment of the present invention.

For example, the processing circuit 20 can determine an audio setting according to the amplitude of the EEG signal measured by the physiological signal sensor 10. Please refer to FIG. 3. FIG. 3 is a schematic diagram of an EEG signal according to an embodiment of the present invention. As shown in FIG. 3, the amplitude of the EEG signal varies according to the current mental state of the user. When the user is in a relaxed state, the amplitude of the EEG signal is smaller than or equal to a threshold value TH1. When the user is in a normal awake state, the amplitude of the EEG signal is between the threshold value TH1 and a threshold value TH2. When the user is in a concentrated or intense state, the amplitude of the EEG signal is greater than or equal to the threshold value TH2. In Step S204, the processing circuit 20 compares the amplitude of the EEG signal with the threshold values TH1 and TH2. In an embodiment, when the processing circuit 20 determines that the amplitude of the EEG signal is smaller than or equal to the threshold value TH1 (e.g., the amplitude of the EEG signal at the interval between time points T3 and T4 shown in FIG. 3), the processing circuit 20 chooses an equalizer setting EQ1 as the audio setting. Further, the processing circuit 20 transmits a first audio selection signal to the audio processing circuit 30 to indicate processing the audio signal by using the equalizer setting EQ1. In another embodiment, when the processing circuit 20 determines that the amplitude of the EEG signal is between the threshold value TH1 and the threshold value TH2 (e.g., the amplitude of the EEG signal at the interval between time points T0 and T1 or between time points T2 and T3 shown in FIG. 3), the processing circuit 20 chooses an equalizer setting EQ2 as the audio setting. Further, the processing circuit 20 transmits a second audio selection signal to the audio processing circuit 30 to indicate processing the audio signal by using the equalizer setting EQ2. In another embodiment, when the processing circuit 20 determines that the amplitude of the EEG signal is greater than or equal to the threshold value TH2 (e.g., the amplitude of the EEG signal at the interval between time points T1 and T2 shown in FIG. 3), the processing circuit 20 chooses an equalizer setting EQ3 as the audio setting. Further, the processing circuit 20 transmits a third audio selection signal to the audio processing circuit 30 to indicate processing the audio signal by using the equalizer setting EQ3.

Figure 4:
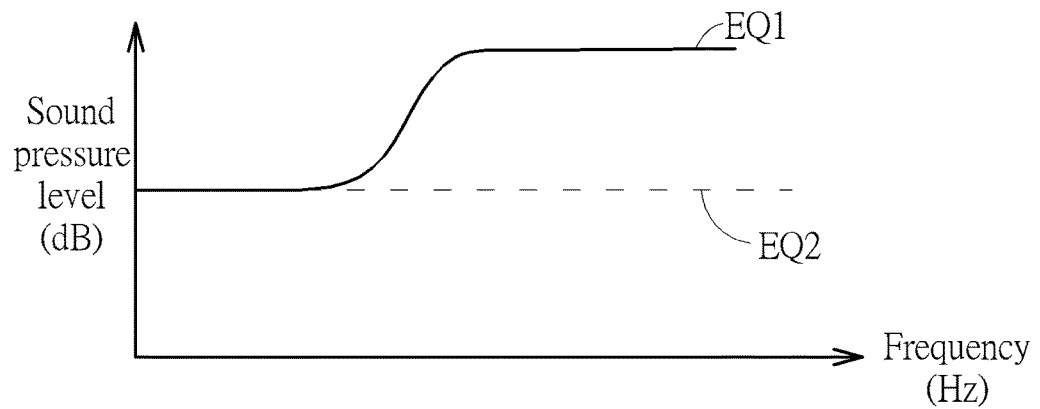
FIGS. 4-6 are schematic diagrams of the audio settings according to embodiments of the present invention.
Figure 5:
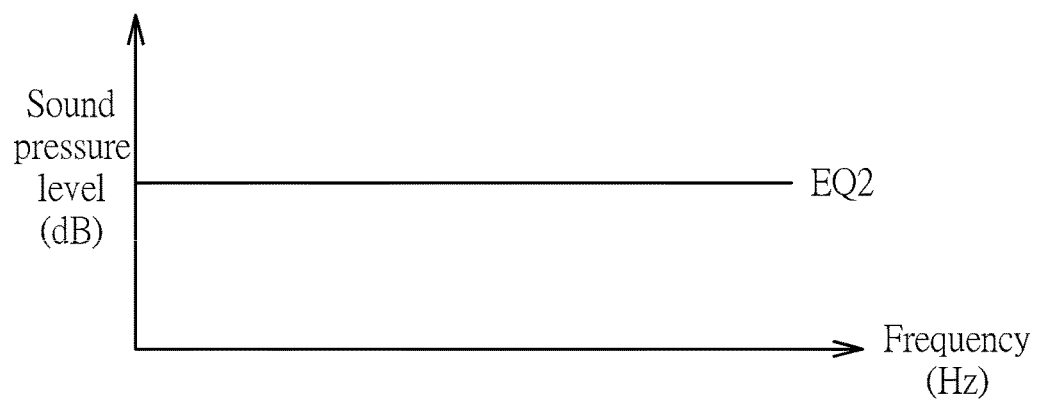
Figure 6:
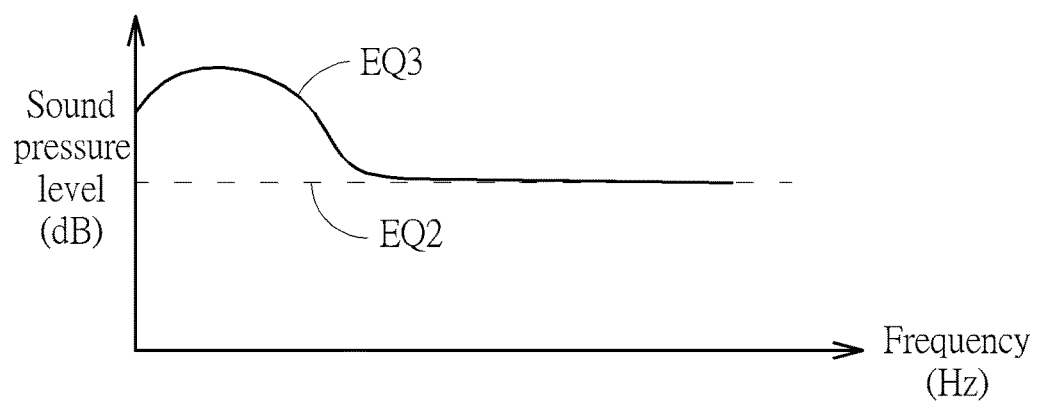

In Step S206, the audio processing circuit 30 receives an audio signal. Further, in response to the audio setting determined by the processing circuit 20, the audio processing circuit 30 adjusts the audio signal according to the audio setting determined by the processing circuit 20 so as to generate an audio output signal. For example, a plurality of audio settings can be stored in the storage device 50. The audio processing circuit 30 can read the audio setting determined by the processing circuit 20 from the storage device 50 and adjusts the audio signal according to the audio setting so as to generate the audio output signal. For example, audio settings EQ1 to EQ3 are stored in the storage device 50. Please refer to FIGS. 4-6. FIGS. 4-6 are schematic diagrams of the audio settings EQ1 to EQ3 according to embodiments of the present invention. Each audio setting may have various sound pressure levels or gains at various frequencies. The audio playback effect may be different for the user when using different equalizer settings. For example, as shown in FIG. 4, compared with the audio setting EQ2 shown in FIG. 5, the audio setting EQ1 shown in FIG. 4 enhances the sound pressure level at high (treble) frequency ranges. The sound pressure level of the audio setting EQ1 at high (treble) frequency ranges shown in FIG. 4 is greater than the sound pressure level of the audio setting EQ2 at high (treble) frequency ranges shown in FIG. 5. As shown in FIG. 6, compared with the audio setting EQ2 shown in FIG. 5, the audio setting EQ3 shown in FIG. 6 enhances the sound pressure level at low (bass) frequency ranges. The sound pressure level of the audio setting EQ3 at low (bass) frequency ranges shown in FIG. 6 is greater than the sound pressure level of the audio setting EQ2 at low (bass) frequency ranges shown in FIG. 5. Therefore, when the processing circuit 20 determines the audio setting EQ1 as the audio setting, the audio processing circuit 30 can adopt the audio setting EQ1 to adjust the audio signal so as to generate the audio output signal corresponding to the audio setting EQ1. When the processing circuit 20 determines the audio setting EQ2 as the audio setting, the audio processing circuit 30 can adopt the audio setting EQ2 to adjust the audio signal so as to generate the audio output signal corresponding to the audio setting EQ2. When the processing circuit 20 determines the audio setting EQ3 as the audio setting, the audio processing circuit 30 can adopt the audio setting EQ3 to adjust the audio signal so as to generate the audio output signal corresponding to the audio setting EQ3.

In Step S208, the audio output circuit 40 receives the audio output signal from the audio processing circuit 30 and plays back the audio output signal for the user. Therefore, when the user is resting and meditating and remains in a relaxed state, the processing circuit 20 determines that the amplitude of the EEG signal is smaller than or equal to the threshold value TH1 and chooses the equalizer setting EQ1 as the audio setting. Accordingly, the audio processing circuit 30 adopts the audio setting EQ1 to adjust the audio signal so as to generate the audio output signal corresponding to the audio setting EQ1. In such a situation, since the mid-high frequency ranges of the sound field effect listened by the user are enhanced, this allows the user to experience a clear, airy and melodious sound field experience. When the user is listening to the radio music and remains in the normal awake state, the processing circuit 20 determines that the amplitude of the EEG signal is between the threshold value TH1 and the threshold value TH2, and chooses the equalizer setting EQ2 as the audio setting. Accordingly, the audio processing circuit 30 adopts the audio setting EQ2 to adjust the audio signal so as to generate the audio output signal corresponding to the audio setting EQ2. Therefore, the sound field effect listened by the user is a nearly a flat frequency response without any modification.

When the user is playing an online game and remains in a concentrated and intense state, the processing circuit 20 determines that the amplitude of the EEG signal is greater than or equal to the threshold value TH2 and chooses the equalizer setting EQ3 as the audio setting. Accordingly, the audio processing circuit 30 adopts the audio setting EQ3 to adjust the audio signal so as to generate the audio output signal corresponding to the audio setting EQ3. In such a situation, since the low-mid frequency ranges of the sound field effect listened by the user are enhanced, this allows the user to experience a strong bass and vivid sound field experience. In other words, embodiments of the electronic system 1 can dynamically adjust sound field effect in real-time according to the current metal state of the user, thus providing a better listening experience for the user.

Figure 7:
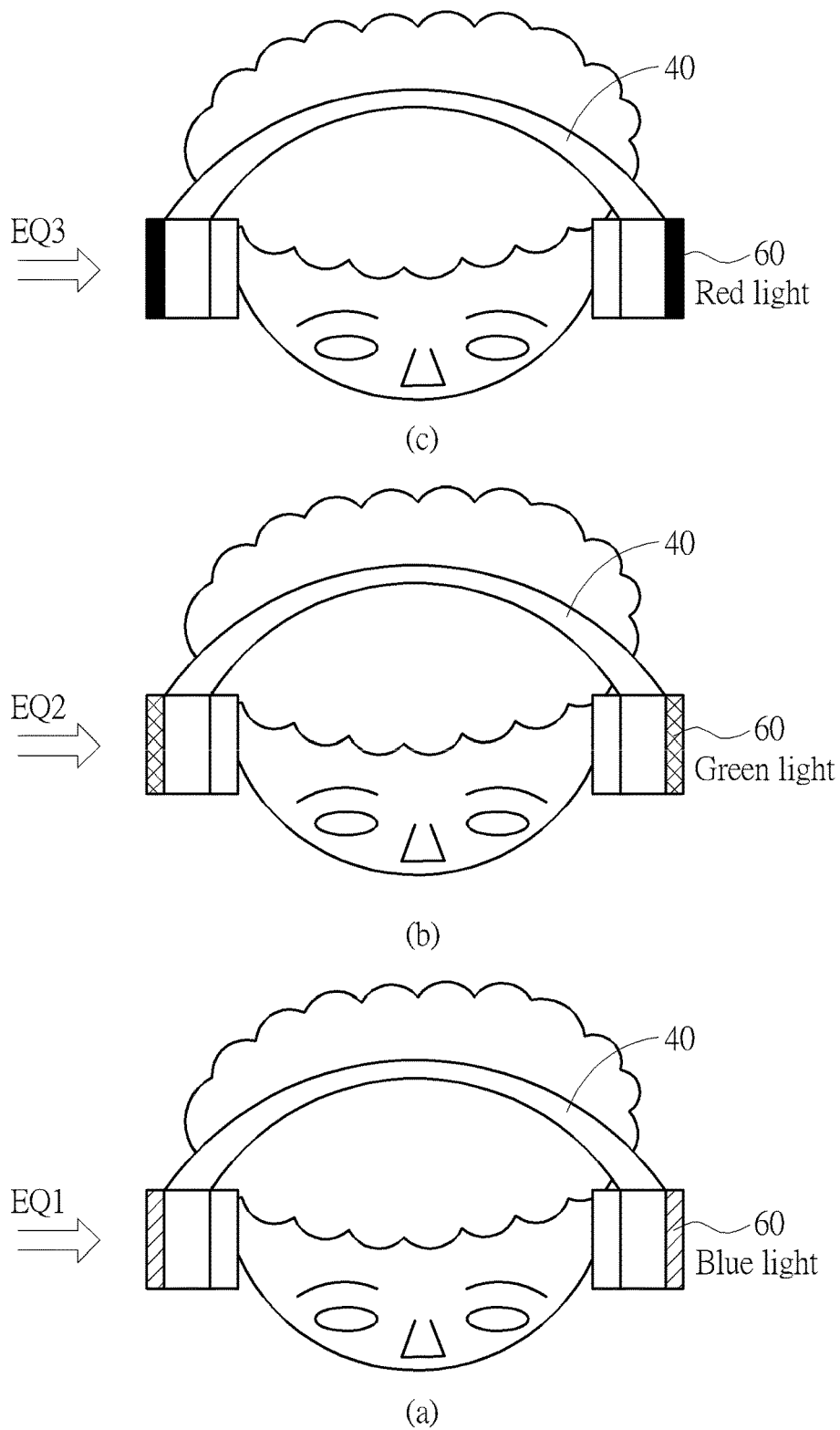
FIG. 7 is a schematic diagram of the indication device during operation according to an embodiment of the present invention.

Moreover, in Step S206, the processing circuit 20 further generates a control signal to the indication device 60 after determining the audio setting. The control signal is utilized to control the indication device 60 to generate an indication signal for informing the user of the current audio setting. For example, the indication device 60 can generate alarm signals (via all kinds of ways, e.g., light, text, sound, voice or vibration) to inform the user. Therefore, in Step S208, via the indication of the indication device 60, the user would immediately know what the audio setting currently utilized by the electronic system 1 is while the audio output circuit 40 plays back the audio output signal for the user. In an embodiment, the indication device 60 can be a light source device. The light source device can be a light emitting diode (LED), an organic light emitting diode (OLED), a micro light emitting diode (μLED) or any other device capable of emitting light. Please refer to FIG. 7. FIG. 7 is a schematic diagram of the indication device 60 during operation according to an embodiment of the present invention. As shown in part (a) of FIG. 7, when determining that the audio setting is the equalizer setting EQ1, the processing circuit 20 generates a first control signal to control the indication device to generate a blue light, so as to inform the user that the current audio setting is the equalizer setting EQ1. As shown in part (b) of FIG. 7, when determining that the audio setting is the equalizer setting EQ2, the processing circuit 20 generates a second control signal to control the indication device to generate a green light, so as to inform the user that the current audio setting is the equalizer setting EQ2. As shown in part (c) of FIG. 7, when determining that the audio setting is the equalizer setting EQ3, the processing circuit 20 generates a third control signal to control the indication device to generate a red light, so as to inform the user that the current audio setting is the equalizer setting EQ3. In addition, the light source device of the indication device 60 can emit light in a continuous manner and/or a flashing manner.

Those skilled in the art should readily make combinations, modifications and/or alterations on the abovementioned description and examples. The abovementioned description, steps, procedures and/or processes including suggested steps can be realized by means that could be hardware, software, firmware (known as a combination of a hardware device and computer instructions and data that reside as read-only software on the hardware device), an electronic system, or combination thereof. Any of the abovementioned procedures and examples above may be compiled into program codes or instructions that are stored in the storage device 50. The processing circuit 20 and the audio processing circuit 30 may read and execute the program codes or the instructions stored in the storage device 50 for realizing the abovementioned functions.

In summary, embodiments of the electronic system can dynamically adjust sound field effect according to the current metal state of the user in real-time, thus providing a better listening experience for the user. Moreover, via the indication of the indication device, the user can immediately know what the audio setting currently utilized by the electronic system is while the audio output circuit plays back the audio output signal for the user.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An electronic system, comprising:
a physiological signal sensor for measuring a physiological signal of a user;
a processing circuit for determining an audio setting according to the physiological signal;
an audio processing circuit for receiving an audio signal and adjusting the audio signal according to the audio setting so as to generate an audio output signal; and
an audio output device for playing the audio output signal;
wherein the physiological signal sensor is an electroencephalogram device and the physiological signal is an electroencephalogram signal, and the processing circuit determines the audio setting according to the amplitude of the electroencephalogram signal;
wherein the processing circuit compares the amplitude of the electroencephalogram signal with a first threshold value and a second threshold value; when determining that the amplitude of the electroencephalogram signal is smaller than or equal to the first threshold value, the processing circuit chooses a first equalizer setting as the audio setting; when determining that the amplitude of the electroencephalogram signal is between the first threshold value and the second threshold value, the processing circuit chooses a second equalizer setting as the audio setting; and when determining that the amplitude of the electroencephalogram signal is greater than or equal to the second threshold value, the processing circuit chooses a third equalizer setting as the audio setting.

2. The electronic system of claim 1, wherein a sound pressure level of the first audio setting at high frequency ranges is greater than a sound pressure level of the second audio setting at high frequency ranges, and a sound pressure level of the third audio setting at low frequency ranges is greater than the sound pressure level of the second audio setting at low frequency ranges.

3. An audio processing method, comprising:
measuring a physiological signal of a user;
determining an audio setting according to the physiological signal, wherein the physiological signal is an electroencephalogram signal, and the step comprises:
comparing the amplitude of the electroencephalogram signal with a first threshold value and a second threshold value;
when determining that the amplitude of the electroencephalogram signal is smaller than or equal to the first threshold value, choosing a first equalizer setting as the audio setting;
when determining that the amplitude of the electroencephalogram signal is between the first threshold value and the second threshold value, choosing a second equalizer setting as the audio setting; and
when determining that the amplitude of the electroencephalogram signal is greater than or equal to the second threshold value, choosing a third equalizer setting as the audio setting;
receiving an audio signal and adjusting the audio signal according to the audio setting so as to generate an audio output signal; and
playing the audio output signal.

4. The audio processing method of claim 3, wherein the a sound pressure level of the first audio setting at high frequency ranges is greater than a sound pressure level of the second audio setting at high frequency ranges, and a sound pressure level of the third audio setting at low frequency ranges is greater than the sound pressure level of the second audio setting at low frequency ranges.

5. An audio processing method, comprising:
  measuring a physiological signal of a user;
  determining an audio setting according to the physiological signal, wherein the physiological signal is an electrocardiogram signal, and the step comprises:
    comparing the amplitude of the electrocardiogram signal with a first threshold value and a second threshold value;
    when determining that the amplitude of the electrocardiogram signal is smaller than or equal to the first threshold value, choosing a first equalizer setting as the audio setting;
    when determining that the amplitude of the electrocardiogram signal is between the first threshold value and the second threshold value, choosing a second equalizer setting as the audio setting; and
    when determining that the amplitude of the electrocardiogram signal is greater than or equal to the second threshold value, choosing a third equalizer setting as the audio setting;
  receiving an audio signal and adjusting the audio signal according to the audio setting so as to generate an audio output signal; and
  playing the audio output signal.

* * * * *